United States Patent [19]
Moore et al.

[11] 3,972,926
[45] Aug. 3, 1976

[54] SUBSTITUTED TRIFLUOROMETHANESULFONANILIDES

[75] Inventors: George G. I. Moore, Birchwood; Joseph Kenneth Harrington, Edina, both of Minn.

[73] Assignee: Riker Laboratories, Inc., St. Paul, Minn.

[22] Filed: June 1, 1972

[21] Appl. No.: 258,832

Related U.S. Application Data

[63] Continuation of Ser. No. 103,803, Jan. 4, 1971, abandoned.

[52] U.S. Cl. .................. 260/556 F; 260/429.9; 260/439 R; 260/448 R; 424/289; 424/295; 424/321
[51] Int. Cl.² .................................. C07C 143/74
[58] Field of Search ......... 260/556 F, 429.9, 439 R, 260/448 R

[56] References Cited
UNITED STATES PATENTS
3,576,866  4/1971  Robertson et al. .............. 260/556 F FOREIGN PATENTS OR APPLICATIONS
1,579,473  7/1969  France............................. 260/556 F
1,188,591  9/1959  France............................. 260/556 F
738,758  10/1955  United Kingdom............. 260/556 F

*Primary Examiner*—Sherman D. Winters
*Attorney, Agent, or Firm*—Alexander, Sell, Steldt & DeLaHunt

[57] ABSTRACT

Substituted trifluoromethanesulfonanilides wherein the anilide ring is bonded to a phenyl ring through a linking group selected from —$CH_2$—, —$CH_2CH_2$—, —$CH(CH_3)$— and

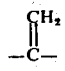

and pharmaceutically acceptable salts thereof. These compounds are active anti-microbial agents.

4 Claims, No Drawings

SUBSTITUTED TRIFLUOROMETHANESULFONANILIDES

This is a continuation of application Ser. No. 103,803, filed Jan. 4, 1971, now abandoned.

This invention relates to substituted trifluoromethanesulfonanilides wherein the anilide ring is bonded to a phenyl ring through a linking group selected from —CH₂—, —CH₂CH₂—, —CH(CH₃)— and

and pharmaceutically acceptable salts thereof. These compounds are active anti-microbial agents and some are also active as anti-inflammatory agents.

Certain substituted trifluoromethanesulfonanilides are known. Thus, such compounds wherein the anilide ring is linked to a phenyl ring through a carbonyl group are known anti-inflammatory agents (see for example British Pat. No. 1,198,301). Such compounds are highly aromatic and resonance stabilized since the two phenyl rings are linked by the pi electron-rich carbonyl group thus providing an extended conjugated system. The compounds of the present invention, on the other hand, have neither an extended conjugated system nor, in general, comparable anti-inflammatory activity. It has been found, however, that they do exhibit a high degree of anti-microbial activity.

Therefore, it is an object of the present invention to provide compounds which are anti-microbial agents.

It is another object of the present invention to provide a method for controlling microorganisms.

It is still another object of the present invention to provide anti-microbial compositions containing one or more substituted trifluoromethanesulfonanilides as active ingredients therein.

Still other objects will be made apparent by the following specification.

DETAILED DESCRIPTION

According to the present invention there is provided a class of compounds of the formula

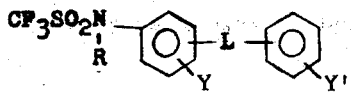

wherein R is hydrogen or a pharmaceutically acceptable cation Y and Y' are independently selected from hydrogen, lower alkyl, lower alkoxy, halogen and nitro and L is a group selected from —CH₂—, —CH₂CH₂—,

and

Lower as used herein refers to groups containing not more than four carbon atoms each.

The compounds of the invention are acidic in nature when R is hydrogen. Consequently, they form salts, i.e. compounds of Formula I wherein R is pharmaceutically acceptable cation. These are generally alkali metal (e.g. lithium, sodium and potassium), alkaline earth metal (e.g. barium, calcium and magnesium), other metal e.g. aluminum, zinc and iron), ammonium and amine salts. Those compounds in which R is an amine cation form a preferred group. The amine salts include the salts of aliphatic (e.g. alkyl), aromatic and heterocyclic amines, as well as those having a mixture of these types of structures. The amines useful in preparing the salts of the invention can be primary, secondary or tertiary and preferably contain not more than 20 carbon atoms.

Preferably, Y and Y' are hydrogen or nitro, most preferably hydrogen. When Y and/or Y' are lower alkyl or lower alkoxy, they are preferably methyl or methoxy. Among the compounds of the invention are the following:

3-(4'-chlorobenzyl)trifluoromethanesulfonanilide
3-(4'-fluorobenzyl)trifluoromethanesulfonanilide
3-[2'-(4-methylphenyl)ethyl]trifluoromethanesulfonanilide
3-(4'-methoxybenzyl)trifluoromethanesulfonanilide
3-benzyl-4-chlorotrifluoromethanesulfonanilide The salts of the invention can be prepared by treating the acid form (wherein R is hydrogen) with a stoichiometrically equivalent amount of an appropriate base under mild conditions. Since many of the salts are water soluble, they are often used in the form of aqueous solutions. Also, they can be used in making pharmaceutical preparations in the form of capsules for oral administration.

The compounds of Formula I wherein R is a hydrogen atom are generally produced by condensation of a trifluoromethanesulfonyl halide or anhydride with a substituted aniline according to the following scheme

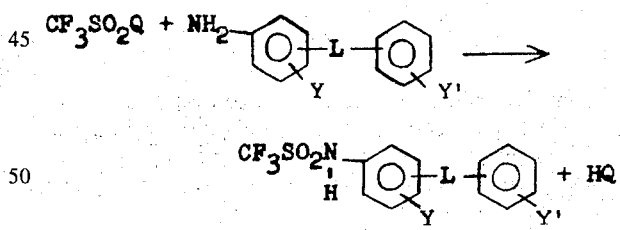

wherein Q represents a halogen atom, preferably chlorine or fluorine, or a corresponding anhydride grouping —OSO₂CF₃ and L, Y and Y' are as previously defined. As will be seen, however, certain of the compounds are preferably prepared using other methods. The intermediates used in preparing the compounds of the invention are known or can be easily prepared from known compounds by well known synthetic methods. Nitro subsituents (Y and/or Y') can be introduced directly in some cases by nitration of compounds of the invention in which Y and/or Y' are hydrogen.

Approximately equivalent amounts of the reactants are brought together at temperatures most often ranging between −15° and 150°C. If necessary or desirable the reaction can be carried out in a pressure vessel. The reaction is preferably but not necessarily carried out in the presence of an acid acceptor such as an alkaline earth or alkali metal carbonate or bicarbonate or a tertiary amine such as pyridine, triethylamine, N,N-dimetylaniline or the like. The amount of acid acceptor can be varied widely; however, a 10 mole percent excess of that amount of base sufficient to bind the liberated strong acid (HQ) is routinely employed.

The condensation is usually conducted in the presence of an appropriate inert organic solvent. Typical solvents suitable for this purpose are dichloromethane, chloroform, carbon tetrachloride, benzene, toluene, bis(2-methoxyethyl)ether, acetonitrile, nitromethane and the like.

After reaction is complete, the product mixture is washed with aqueous hydrochloric acid, the solvent is evaporated in vacuo and the residue is dissolved in a dilute aqueous base solution which is washed with dichloromethane and treated with decolorizing charcoal. The product, in the form of a salt which is usually soluble in the basic aqueous layer is precipitated therefrom by addition of a mineral acid such as hydrochloric or sulfuric acid, and collected by filtration or extraction with dichloromethane.

The compounds of the invention wherein the connecting link is —CH$_2$— can also be prepared by reduction of the known benzoyltrifluoromethanesulfonanilides, using hydrazine hydrate-potassium hydroxide, zinc amalgam in acid, etc. as the reducing agents.

Those compounds wherein the connecting link is —CH$_2$CH$_2$— can be prepared by the reduction of trifluoromethanesulfonamidostilbenes (in which L is vinylene (—CH=CH—) or corresponding compounds wherein L is

or

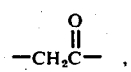, using hydrazine hydrate-potassium hydroxide or zinc amalgam in acid as the reducing agent. The intermediate stilbenes are prepared by condensing together a trifluoromethanesulfonylhalide or the anhydride with the aniline derivative

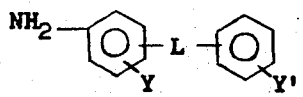

in which L is vinylene and Y and Y' are as previously defined. This reaction is most often carried out at −15° to 150°C. in the presence of an acid acceptor and an inert solvent. The intermediate compounds (mentioned above) in which the connecting link is

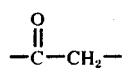

are prepared by oxidation of the corresponding compounds wherein the linkage group is

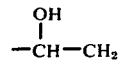

(which are, in turn, preferably prepared by condensation of formyltrifluoromethanesulfonanilides with benzyl magnesium chloride in a suitable solvent such as tetrahydrofuran).

Compounds of the invention wherein the connecting link is

may also be prepared by reduction of compounds wherein L is

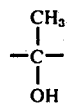

with hydroiodic acid and red phosphorus. Intermediates wherein L is

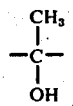

are prepared from known compounds wherein L is

by a Grignard reaction with methyl magnesium bromide.

Compounds of the invention wherein L is

are prepared by reaction of intermediates wherein L is

with methyl magnesium iodide followed by hydrochloric acid treatment as shown in the examples.

The salts of the invention are readily prepared by adding the stoichiometric amount of the selected base in inert solvent solution (aqueous or nonaqueous) to the acidic compound. The resulting solution is treated to remove the solvent, e.g. by evaporation under reduced pressure, to obtain the salt, usually as a dry powder. Appropriate bases for use in preparing the metal salts include metal oxides, carbonates, hydroxides, bicarbonates and alkoxides. The organic amine salts and the ammonium salts can be prepared by reacting the acid form with the appropriate organic base or ammonium hydroxide. Some salts are also prepared by cation exchange reactions (by reacting a salt of the invention with an organic or inorganic salt in a cation exchange reaction).

As noted previously the compounds of the invention are as a class anti-microbial agents, although some are more active than others. The anti-microbial activity can be conveniently demonstrated using a variation of the original agar-plate diffusion method of Vincent and Vincent. The culture media employed are designed to meet the minimum essential requirements for the growth of the various test organisms. They are based on the synthetic glucose-salts medium of Davis and Mingioli (DG-agar). The table below gives the media used for each of the test oganisms:

| Organism | Medium |
|---|---|
| 1. Staphylococcus aureus | DGY |
| 2. Bacillus subtilus | DGA |
| 3. Pseudomonas aeruginosa | DG |
| 4. Escherichia coli | DG |
| 5. Streptococcus sp.* | * |
| 6. Aspergillus niger | DG |
| 7. Candida albicans | DGY |

*Strains isolated from dental caries in rats or hamsters at the National Institute of Dental Health and grown in PFY or APT agar.

The agar media are melted in a steam bath, supplements, if any, are added, and the media are cooled to 42° C. in a water bath. Then from $10^4$ to $10^5$ cells or spores of the test organism are added per 10 ml. of agar, and the media are dispensed, at 10 ml. per dish, into 9 cm. circular plastic petri dishes.

The tests are carried out quantitatively by placing 4 $\mu$l. aliquots of 1 percent, 0.1 percent and 0.01 percent solution of the test chemicals on 6.5 mm. paper discs to give 40, 4.0 and 0.4 $\mu$g. per disc, respectively.

For the first part of the tests, in serum-free media, the same culture media are used as described above. For the second part of the tests, all test organisms except number 5, are grown in PGY agar supplemented with 10 percent horse serum. Organism number 5 is grown in APT agar supplemented with 10 percent horse serum in a desiccator in 10 percent $CO_2$ in air. The others (1,2,3,4, 6 and 7) are grown in air. Plates are incubated at 30° C. for 24 hours (for bacteria and *C. albicans*) and 48 hours for *A. niger*. The diameters of the zones of inhibition are measured, and log m is plotted against $X^2$, where m is the weight of test compound on the disc in $\mu$g. and X is the diameter of the zone of inhibition in mm.

The culture media used in the foregoing tests are as follows:

| DG: | $K_2HPO_4$ | 7.0 g. |
| | $NaH_2PO_4.H_2O$ | 2.3 g. |
| | $MgSO_4.7H_2O$ | 0.1 g. |
| | $(NH_4)_2SO_4$ | 1.0 g. |
| | $CaCl_2.2H_2O$ | 0.04 g. |
| | $FeSO_4.7H_2O$ | 0.01 g. |
| | Dextrose | 2.0 g. |
| | Ionagar | 8.5 g. |
| | Dist. Water | 1 liter |
| DGY: | DG supplemented with 1 g. per liter of yeast extract | |
| DGA: | DG supplemented with 600 mg./l. glutamic acid 200 mg./l. cystine 800 mg./l. asparagine 20 mg./l. EDTA disodium | |

| PGY: | NaCl | 16.0 g. |
| | KCl | 0.80 g. |
| | $MgSO_4.7H_2O$ | 0.308 g. |
| | $CaCl_2.2H_2O$ | 0.032 g. |
| | $Na_2HPO_4.7H_2O$ | 0.58 g. |
| | $KH_2PO_4$ | 0.30 g. |
| | Phenol Red | 0.0024 g. |
| | Yeast Extract | 2.0 g. |
| | $Na_2HPO_4$ | 0.307 g. |
| | Glucose | 4.0 g. |
| | Ionagar | 8.50 g. |
| | Dist. Water | 1 liter |
| APT: | Trypticase | 8.5 g. |
| | Yeast Extract | 7.5 g. |
| | Sodium Chloride | 5.0 g. |
| | Potassium Phosphate | 5.0 g. |
| | Sodium Citrate | 5.0 g. |
| | Dextrose | 10.0 g. |
| | Polysorbate 80 | 0.2 g. |
| | Magnesium Sulfate | 0.8 g. |
| | Manganous Chloride | 0.14 g. |
| | Ferrous Sulfate | 0.04 g. |
| | Sodium Carbonate | 1.25 g. |
| | Agar | 13.5 g. |

Leading references to the method used are: Vincent, J. G., and Vincent, Helen W., Proc. Soc, Exptl. Biol. Med. 55:162–164, 1944, and Davis, B. D., and Mingioli, E. S., Jour. Bact. 66:129–136, 1953.

Presently preferred compounds of the invention are 3-benzyltrifluoromethanesulfonanilide,
4-(2'-phenethyl)trifluoromethanesulfonanilide and
2-(2'-phenethyl)trifluoromethanesulfonanilide.

These compounds are preferred because of their broader spectrum of anti-microbial activity. All are active against *staphylococcus aureus, streptococcus sp.* and *bacillus subtilus,* as well as other microorganisms. Such anti-microbial agents are useful for disinfecting and sterilizing medical and dental equipment as components of disinfecting solutions.

Certain of the compounds of the present invention are also active anti-inflammatory agents. The anti-inflammatory activity can be conveniently demonstrated using assays designed to test the ability of these compounds to antagonize local edema, which is a characteristic of the anti-inflammatory response (rat foot edema test), and to inhibit the onset of the erythematous manifestation of inflammation (guinea pig erythema test).

These are standard assays well known to those skilled in the art. They are described in journals and other publications. Leading references to the rat foot edema test are:

1. Adamkiewica et al., Canad. J. Biochem. Physic. 33:332, 1955;

2. Selye, Brit. Med. J. 2:1129, 1949; and
3. Winter, Proc. Soc. Exper. Biol. Med. 111:544, 1962

Leading references to the guinea pig erythema test are:

1. Wilhelmi, Schweiz. Med. Wschr. 79:577, 1949, and
2. Winder et al., Arch. Int. Pharmacodyn. 116:261, 1958.

The anti-inflammatory activity of various compounds of the invention may be detected by other standard assays known to the art such as the cotton pellet granuloma and adjuvant arthritis tests.

The compounds are administered orally, for example as four percent acacia suspensions, but may also be administered parenterally. Amounts are generally about 1 to 500 mg./kg. of body weight of the mammal to be treated.

The following examples are given for the purpose of further illustrating the procedures used in the present invention, but are not intended, in any way, to be limiting on the scope thereof. Thus, while the majority of the examples relate to compounds in the acid form (that is having a hydrogen atom bonded to the sulfonamido nitrogen) it is understood that the salts are likewise contemplated. The salts, which have a cation bonded to the sulfonamido nitrogen, generally have the utility areas of the corresponding acid form compounds. All melting points are uncorrected and are given in degrees Centigrade.

EXAMPLE 1

A slurry of aluminum chloride (34.0 g., 0.25 mole) in benzene (200 ml.) at 60° C. is treated with 3-nitrobenzyl chloride (43 g., 0.25 mole) in benzene (200 ml.) causing darkening and evolution of gas. The mixture is cooled, poured into a mixture of ice and hydrochloric acid and the layers are separated. The organic layer is dried, then concentrated in vacuo to an oil, 3-nitrodiphenylmethane.

The 3-nitrodiphenylmethane (56 g.) is reduced by refluxing with sodium sulfide (0.25 mole) in 95 percent aqueous ethanol for four hours. The solution is diluted with water and extracted with chloroform, then extracted with 15 percent hydrochloric acid. The acid extracts are treated with ammonium hydroxide to give 3-aminodiphenylmethane, m.p. 44°–46° C.

A solution of 3-aminodiphenylmethane (19.0 g., 0.104 mole) is dissolved in chloroform (250 ml.) and triethylamine (14.3 ml.) and treated with trifluoromethanesulfonic anhydride (17.4 ml., 0.104 mole).

The solution is washed with dilute hydrochloric acid, then with dilute sodium hydroxide solution. The basic aqueous layer is extracted with chloroform and treated with decolorizing charcoal, then acidified to give an oil. The oil is distilled at 154°–162° C./0.25 mm. It slowly crystallizes with cooling and scratching and is recrystallized from petroleum ether to give 3-benzyltrifluoromethanesulfonanilide, m.p. 39°–40° C.

| Analysis | %C | %H |
|---|---|---|
| Calculated for $C_{14}H_{12}F_3NO_2S$: | 53.4 | 3.8 |
| Found: | 53.5 | 3.9 |

EXAMPLE 2

The reactions of this example use the procedures of Example 1. 2-Nitrobenzyl chloride is reacted with benzene to give 2-nitrodiphenylmethane which is reduced to 2-aminodiphenylmethane. The 2-aminodiphenylmethane is reacted with trifluoromethanesulfonic anhydride to give 2-benzyltrifluoromethanesulfonanilide, m.p. 55°–56.5° C.

| Analysis | %C | %H | %N |
|---|---|---|---|
| Calculated for $C_{14}H_{12}F_3NO_2S$: | 53.4 | 3.8 | 4.4 |
| Found: | 53.4 | 3.8 | 4.4 |

2-Benzyltrifluoromethanesulfonanilide is dissolved in acetic acid and treated with an equimolar amount of 70% nitric acid. Two drops of sulfuric acid are added and the mixture is heated on a steam bath for 2.5 hours and cooled. It is then poured into ice water and the solid product is separated by filtration and recrystallized to give 2-benzyl-4-nitrotrifluoromethanesulfonanilide, m.p. 74°–75° C.

EXAMLE 3

A solution of methyl magnesium iodide in prepared from magnesium (2.4 g.) and methyl iodide (14.1 g.) in diethyl ether. To this solution is added sodium 3-benzoyltrifluoromethanesulfonanilide (26.3 g., 0.075 mole) in tetrahydrofuran solution. An excess of ten percent hydrochloric acid is added and the layers are separated. The organic layer is dried over magnesium sulfate, filtered, then evaporated in vacuo. The residue is dissolved in ten percent sodium hydroxide, then the solution is neutralized with ten percent hydrochloric acid to give the product as a separate liquid layer. When this layer is distilled, b.p. 153° C./0.18 mm. the product solidifies. Recrystallization twice from petroleum ether gives 1-phenyl-1-(3-trifluoromethanesulfonamidophenyl)-ethylene, m.p. 55°–59° C.

| Analysis | %C | %H | %N |
|---|---|---|---|
| Calculated for $C_{15}H_{12}F_3NO_2S$: | 55.1 | 3.7 | 4.3 |
| Found: | 54.8 | 3.9 | 4.2 |

EXAMPLE 4

Methyl magnesium bromide (0.075 mole) in tetrahydrofuran is treated with sodium 3-benzoyltrifluoromethanesulfonanilide (16.3 g., 0.046 mole) in tetrahydrofuran. After stirring three hours the mixture is concentrated by evaporation in vacuo, the residue is treated with ten percent sulfuric acid and extracted with diethyl ether and dichloromethane. The organic layers are combined, dried over magnesium sulfate, filtered and evaporated in vacuo. The residue is an oil, 3-(1′-phenyl-1′-hydroxyethyl)trifluoromethanesulfonanilide. It may be isolated as the triethylammonium salt (m.p. 124°–126° C.) or used without purification for the next step.

3-(1′-Phenyl-1′-hydroxyethyl)trifluoromethanesulfonanilide (6.90 g., 0.020 mole) is placed in acetic acid (20 ml.) and heated with a mixture of 55 percent hydroiodic acid (20 ml., stabilized with phosphorus acid) and red phosphorus (2.4 g., 0.08 mole) at 100° to 110°

C. for three hours. The cooled solution is filtered, diluted with water, then extracted with dichloromethane. The extracts are dried over magnesium sulfate, filtered and evaporated in vacuo. The residue, an oil, is distilled, b.p. 151° C./0.27 mm. The product solidifies on scratching in cold petroleum ether. After recrystallizing twice from petroleum ether solid 3-(1-phenethyl)-trifluoromethanesulfonanilide, m.p. 38°–41° C., is obtained.

| Analysis | %C | %H | %N |
|---|---|---|---|
| Calculated for $C_{15}H_{14}F_3NO_2S$: | 54.8 | 4.3 | 4.3 |
| Found: | 54.7 | 4.3 | 4.2 |

EXAMPLE 5

The triphenylphosphonium salt of benzyl chloride (38.9 g., 0.10 mole) is added to a solution of sodium (3.0 g.) in ethanol (200 ml.). The resulting solution is treated with 2-nitrobenzaldehyde (16 g., 0.10 mole) and stirred overnight. The mixture is filtered, washed with water and extracted with dichloromethane. The extracts are evaporated to a dark residue which is extracted with carbon tetrachloride, then these extracts are concentrated and passed through a column of alumina, eluting with hexane and carbon tetrachloride to give a yellow oil, 2-nitrostilbene.

2-Nitrostilbene (19.3 g.) is reduced with Raney nickel in ethanol at about 40 p.s.i. of hydrogen and the product is 2-(2'-phenethyl)aniline, a tan liquid.

2-(2'-Phenethyl)aniline (15.1 g., 0.077 mole) is dissolved in dichloromethane and triethylamine (12 ml.) is added followed by trifluoromethanesulfonic anhydride (13 ml., 0.077 mole). The solution is then evaporated in vacuo, the residue is dissolved in dilute sodium hydroxide and the solution is filtered through decolorizing charcoal. Acidification with concentrated hydrochloric acid gives a solid which is separated by filtration and recrystallized thrice from a hexane-chloroform mixture, filtering with decolorizing charcoal. The product, 2-(2'-phenethyl)trifluoromethanesulfonanilide, is a white solid, m.p. 62°–64° C.

| Analysis | %C | %H | %N |
|---|---|---|---|
| Calculated for $C_{15}H_{14}F_3NO_2S$: | 54.8 | 4.3 | 4.3 |
| Found: | 55.0 | 4.3 | 4.1 |

EXAMPLE 6

Using the procedure of Example 5 benzyltriphenylphosphonium chloride (0.1 mole) and 4-nitrobenzaldehyde (0.1 mole) are reacted to give 4-nitrostilbene. The 4-nitrostilbene is reduced with palladium on charcoal as the catalyst to 4-(2'-phenethyl)aniline, m.p. 46°–50° C.

Sulfonylation is carried out as in Example 5 to give a solid product. Recrystallization from a mixture of hexane and petroleum ether gives white crystals of 4-(2'-phenethyl)trifluoromethanesulfonanilide, m.p. 71°–73° C.

| Analysis | %C | %H | %N |
|---|---|---|---|
| Calculated for $C_{15}H_{14}F_3NO_2S$: | 54.8 | 4.3 | 4.3 |

| Analysis | %C | %H | %N |
|---|---|---|---|
| Found: | 54.9 | 4.3 | 4.1 |

EXAMPLE 7

To a round-bottomed flask containing trans-3-aminostilbene (3.34 g., 17.1 mmole) dissolved in dichloromethane (25 ml.) and triethylamine (2.7 ml., 1.95 g., 19.3 mmole) is added trifluoromethanesulfonic anhydride (2.9 ml., 4.9 g., 17.3 mmole) with stirring and external cooling (ice bath). The mixture is made basic with sodium hydroxide solution, then steam distilled to remove triethylamine and other volatile impurities. The residue is then acidified with hydrochloric acid and the solvent is removed in vacuo to give solid trans-3-(trifluoromethanesulfonamido)stilbene which is recrystallized twice from hexane-trichloroethylene to give an analytical sample, m.p. 62°–64° C.

| Analysis | %C | %H | %N |
|---|---|---|---|
| Calculated for $C_{15}H_{12}F_3NO_2S$: | 55.1 | 3.7 | 4.3 |
| Found: | 55.3 | 3.7 | 4.3 |

A solution of trans 3-(trifluoromethanesulfonamido)-stilbene (7.3 g., 0.022 mole) in ethanol is reduced with hydrogen at 45 p.s.i. and five percent palladium on charcoal as catalyst. The solution is then filtered and evaporated in vacuo to a tan oil. The oil is dissolved in diisopropyl ether and stirred with excess triethylamine. Several recrystallizations of the product from an isopropanol-diisopropyl ether mixture give white solid, triethylammonium 3-(2'-phenethyl)trifluoromethanesulfonanilide, m.p. 82°–85.5° C.

| Analysis | %C | %H | %N |
|---|---|---|---|
| Calculated for $C_{15}H_{14}F_3NO_2S \cdot C_6H_{15}N$: | 58.7 | 6.8 | 6.5 |
| Found: | 58.8 | 6.7 | 6.4 |

EXAMPLE 8

Using the procedure of Example 5 benzyltriphenylphosphonium chloride and 3-nitrobenzaldehyde are reacted to give 3-nitrostilbene which is selected to 3-aminostilbene. The 3-aminostilbene is sulfonylated to give 3-(2'-phenethyl)trifluoromethanesulfonanilide, m.p. 64.5°–66° C.

| Analysis | %C | %H | %N |
|---|---|---|---|
| Calculated for $C_{15}H_{14}F_3NO_2S$: | 54.8 | 4.3 | 4.3 |
| Found: | 55.1 | 4.3 | 4.2 |

What is claimed is:
1. A compound of the formula

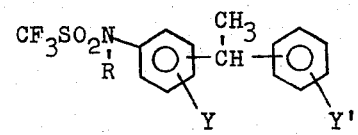

wherein R is hydrogen or a pharmaceutically acceptable cation and Y and Y' are independently selected from hydrogen, lower alkyl, lower alkoxy, halogen and nitro.

2. A compound of the formula

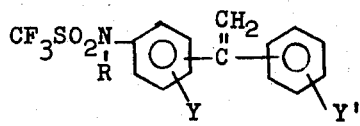

wherein R is hydrogen or a pharmaceutically acceptable cation and Y and Y' are independently selected from hydrogen, lower alkyl, lower alkoxy, halogen and nitro.

3. 3-(1-Phenethyl)trifluoromethanesulfonanilide according to claim 1.

4. 1-Phenyl-1-(3-trifluoromethanesulfonamidophenyl) ethylene according to claim 2.

* * * * *